United States Patent
Ross et al.

(10) Patent No.: US 10,124,076 B2
(45) Date of Patent: Nov. 13, 2018

(54) IMAGING AGENTS AND METHODS OF USE THEREOF

(71) Applicant: Huntington Medical Research Institutes, Pasadena, CA (US)

(72) Inventors: Brian D. Ross, Altadena, CA (US); Pratip Bhattacharya, Pasadena, CA (US)

(73) Assignee: HUNTINGTON MEDICAL RESEARCH INSTITUTES, Pasadena, CA (US)

( * ) Notice: Subject to any disclaimer, the term of this patent is extended or adjusted under 35 U.S.C. 154(b) by 0 days.

(21) Appl. No.: 13/778,887

(22) Filed: Feb. 27, 2013

(65) Prior Publication Data

US 2014/0065073 A1    Mar. 6, 2014

Related U.S. Application Data

(63) Continuation of application No. 12/522,443, filed as application No. PCT/US2008/050932 on Jan. 11, 2008, now abandoned.

(60) Provisional application No. 60/884,590, filed on Jan. 11, 2007.

(51) Int. Cl.
| | |
|---|---|
| *A61K 49/10* | (2006.01) |
| *G01N 24/08* | (2006.01) |
| *G01R 33/28* | (2006.01) |
| *G01R 33/56* | (2006.01) |
| *G01R 33/46* | (2006.01) |
| *G01R 33/48* | (2006.01) |

(52) U.S. Cl.
CPC ............. *A61K 49/10* (2013.01); *G01N 24/08* (2013.01); *G01R 33/282* (2013.01); *G01R 33/5601* (2013.01); *G01R 33/4608* (2013.01); *G01R 33/4806* (2013.01)

(58) Field of Classification Search
CPC .. A61K 49/10; G01R 33/5601; G01R 33/282; G01R 33/4608; G01R 33/4806; G01N 24/08
USPC .......................................... 424/9.3; 600/420
See application file for complete search history.

(56) References Cited

U.S. PATENT DOCUMENTS

| | | | |
|---|---|---|---|
| 5,492,814 A | 2/1996 | Weissleder | |
| 5,726,571 A | 3/1998 | Guclu et al. | |
| 5,965,133 A | 10/1999 | Cantor et al. | |
| 6,008,644 A | 12/1999 | Leunbach et al. | |
| 6,108,574 A | 8/2000 | Ardenkjaer-Larsen et al. | |
| 6,278,893 B1 | 8/2001 | Ardenkjaer-Larsen et al. | |
| 6,311,086 B1 | 10/2001 | Ardenkjaer-Larsen et al. | |
| 6,453,188 B1 | 9/2002 | Ardenkjaer-Larsen et al. | |
| 6,466,814 B1 | 10/2002 | Ardenkjaer-Larsen et al. | |
| 6,574,495 B1 | 6/2003 | Golman et al. | |
| 6,574,496 B1 | 6/2003 | Golman et al. | |
| 6,711,440 B2 | 3/2004 | Deal et al. | |
| 6,727,697 B2 | 4/2004 | Fiat | |
| 7,256,047 B2 | 8/2007 | Malloy et al. | |
| 2002/0137965 A1 | 9/2002 | Axelsson et al. | |
| 2003/0124732 A1 | 7/2003 | Axelsson et al. | |
| 2003/0157020 A1 | 8/2003 | Petersson et al. | |
| 2003/0212323 A1 | 11/2003 | Petersson et al. | |
| 2004/0024307 A1 | 2/2004 | Golman et al. | |
| 2004/0066193 A1 | 4/2004 | Ardenkjaer-Larsen et al. | |
| 2004/0171928 A1 | 9/2004 | Petersson et al. | |
| 2006/0104906 A1 | 5/2006 | Ardenkjaer-Larsen et al. | |
| 2006/0127313 A1 | 6/2006 | Goldman et al. | |
| 2006/0173283 A1 | 8/2006 | Axelsson et al. | |
| 2007/0025918 A1 | 2/2007 | Hurd | |
| 2007/0140966 A1 | 6/2007 | Chang et al. | |
| 2008/0260649 A1 | 10/2008 | Thaning et al. | |
| 2009/0264732 A1 | 10/2009 | Ross et al. | |

FOREIGN PATENT DOCUMENTS

| | | |
|---|---|---|
| WO | 2004/019996 A1 | 3/2004 |
| WO | 2004/019997 A1 | 3/2004 |
| WO | 2004/090563 A1 | 10/2004 |
| WO | 2006/011809 A1 | 2/2006 |
| WO | 2006/011810 A3 | 2/2006 |
| WO | 2006/011811 A3 | 2/2006 |
| WO | 2006/054903 A3 | 5/2006 |

(Continued)

OTHER PUBLICATIONS

International PCT Search Report and Written Opinion dated Jan. 18, 2008 for PCT/US06/39974.

(Continued)

*Primary Examiner* — Michael G Hartley
*Assistant Examiner* — Leah H Schlientz
(74) *Attorney, Agent, or Firm* — Hahn Loeser & Parks, LLP

(57) ABSTRACT

Compositions and methods useful in connection with magnetic resonance imaging are provided. Metabolites hyperpolarized by dynamic nuclear polarization are used as reporter molecules in nuclear magnetic resonance ("NMR") spectroscopy to study metabolic pathways and diagnose disease states. The reporter molecules include hyperpolarized glutamine and hyperpolarized acetate. The invention includes the reporter molecules, compositions including the reporter molecules in pharmaceutically acceptable carriers, methods for studying metabolic pathways that include introducing one or more of the reporter molecules to a mammalian subject and imaging a target substance using NMR spectroscopy, and kits useful in studying metabolic pathways that incorporate one or more of the reporter molecules and instructions for their use.

4 Claims, 12 Drawing Sheets

(56) References Cited

FOREIGN PATENT DOCUMENTS

| WO | 2007/044867 A3 | 4/2007 |
| WO | 2008/086534 A1 | 7/2008 |
| WO | 2009/046457 A3 | 4/2009 |
| WO | 2009/129265 A1 | 10/2009 |

OTHER PUBLICATIONS

International Preliminary Report on Patentability dated Apr. 7, 2009 for PCT/US06/39974.

International PCT Search Report and Written Opinion dated May 20, 2008 for PCT/US08/50932.

International Preliminary Report on Patentability dated Jul. 14, 2009 for for PCT/US08/50932.

International PCT Search Report and Written Opinion dated Aug. 18, 2009 for PCT/US08/78999.

International Preliminary Report on Patentability dated Apr. 7, 2010 for PCT/US08/78999.

International PCT Search Report and Written Opinion dated Jun. 9, 2009 for PCT/US09/40568.

Golman, K. et al., "Molecular imaging with endogenous substances," PNAS, vol. 100, No. 18, pp. 10435-01439 (Sep. 2, 2003).

Bowers, C.R. and Weitekamp, D.P., Transformation of symmetrization order to nuclear-spin magnetization by chemical reaction and nuclear magnetic resonance, Phys. Rev. Lett., 57(21):2645-2648 (1986).

Bowers, C.R. and Weitekamp, D.P., Parahydrogen and Synthesis Allow Dramatically Enhanced Nuclear Alignment, J. Am. Chem. Soc., 109:5541-5542 (1987).

Golman, K. et al., Parahydrogen-induced polarization in imaging: subsecond (13)C angiography, Magn. Reson. Med., 46:1-5 (2001).

Ardenkjaer-Larsen, J.H. et al., Increase in signal-to-noise ratio of > 10,000 times in liquid-state NMR, Proc. Natl. Acad. Sci. USA, 100(18):10158-63 (2003).

Johannesson, H. et al., Transfer of para-hydrogen spin order into polarization by diabatic field cycling, C. R. Physique, 5:315-324 (2004).

Forsen, S. and Hoffman, R.A., Study of moderately rapid exchange reaction by means of nuclear magnetic double resonance, J. Chem. Phys., 39: 2892-2901 (1963).

Golman, K. et al., Molecular imaging using hyperpolarized 13C, British J. of Radiol., 76: S118-S127 (2003).

Bhattacharya, P. et al., Ultra fast three dimensional imaging of hyperpolarized 13C in Vivo. MAGMA, 18.5, 245-256 (2005).

Fayad, Z.A. et al., Serial, noninvasive, in vivo magnetic resonance microscopy detects the development of atherosclerosis in apolipoprotein E-deficient mice and its progression by arterial wall remodeling, J. Magn. Reson. Imag., 17(2):184-189 (2003).

Snapper, I. et al., Pharmacology and therapeutic value of diamidine derivatives, particularly of 2-hydroxystilbamidine, Trans. NY Acad. Sci., 14(7):269-271 (1952).

Schmued, L.C. et al., Intracranial injection of Fluoro-Gold results in the degeneration of local but not retrogradely labeled neurons, Brain Res., 626(1-2):71-77 (1993).

167B(2.40mg 15N choline chloride)
Poi=4h

IMAGING AGENTS AND METHODS OF USE THEREOF

CROSS-REFERENCE TO RELATED APPLICATIONS

This application is a continuation of U.S. Ser. No. 12/522,443, filed Jul. 8, 2009, currently pending, which is a National Phase of International Application No. PCT/US08/050932, filed Jan. 11, 2008, which designated the U.S. and that International Application was published under PCT Article 21(2) in English, now expired, which claims the priority benefit of U.S. provisional application No. 60/884,590, filed Jan. 11, 2007, the contents of all of which are herein incorporated by reference in their entirety.

FIELD OF INVENTION

The invention relates to compositions and methods useful in connection with magnetic resonance imaging. In particular, the invention relates to Dynamic Nuclear Polarization ("DNP") hyperpolarization of metabolites for nuclear magnetic resonance ("NMR") spectroscopy and magnetic resonance imaging ("MRI").

BACKGROUND OF THE INVENTION

Magnetic resonance ("MR") imaging has become a well-accepted and commonly-used technique for studying a wide range of physiologic processes. This technology is useful in connection with disease diagnosis and prognosis, and in the broader study of biological systems. Indeed, many hospitals and medical facilities have MR imaging equipment on-site, and routinely make use of it to aid in the diagnoses and monitoring of an array of diseases and physiologic conditions. Contrast agents or reporter molecules are used in connection with MR imaging, and a wide range of products is commercially available to image various systems. Along these lines, there remains a strong need in the art for improved reporter molecules for use in connection with MR imaging for a wide range of diseases and physiologic conditions.

It is remarkable that NMR has contributed so much to our understanding of the brain and other organs using only part-per-million polarizations. That MRI is possible at all is due to slight variations in the density or relaxation times of the highly concentrated (~80 M) water protons. The in vivo study of metabolism with $^1$H, $^{13}$C or $^{15}$N NMR by previous methods has been possible only with little or no spatial localization and prolonged signal averaging that largely precludes the study of dynamics and is severely limited by cost.

The Boltzmann distribution leads to low signal to nose ration (SNR) in NMR spectroscopy. This has been accommodated in the application of NMR spectroscopy to analytical chemistry by using concentrated samples and signal averaging. However, in biology, NMR spectroscopy has yet to reach its full potential for the simple season of time limitation associated with high number of transients required to obtain sufficient SNR under the biological constraints of low concentration, physiological temperature, and high dielectric losses. Nowhere is this more relevant than in the brain, where neurochemical events occur on the spatial and temporal scale of electrical neurotransmission (second to milliseconds).

DESCRIPTION OF THE FIGURES

Exemplary embodiments are illustrated in referenced figures. It is intended that the embodiments and figures disclosed herein are to be considered illustrative rather than restrictive.

SUMMARY OF THE INVENTION

Figure 1:
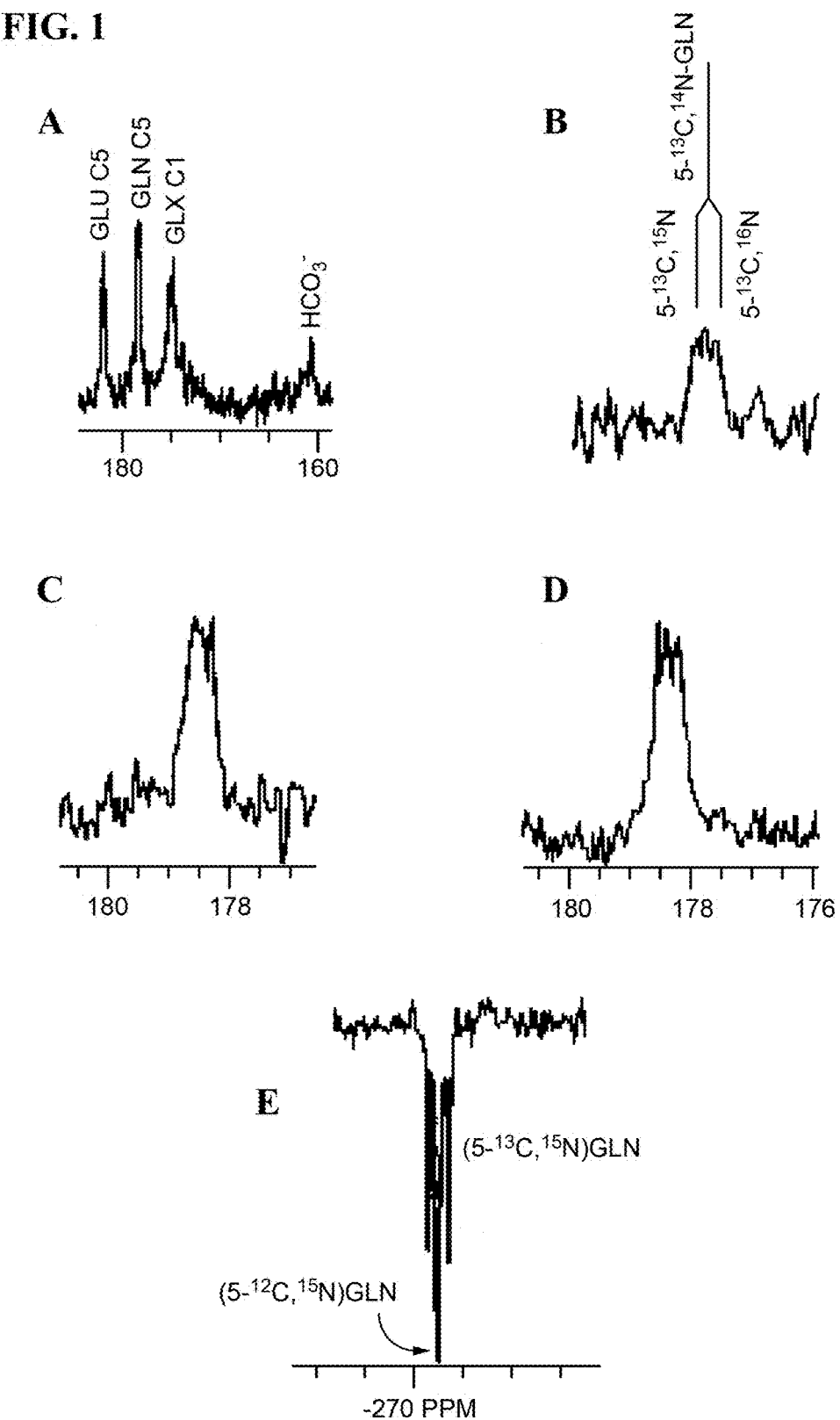
FIG. 1. Metabolic fate of $^{13}C_2$-$C_5$-Glucose in rat brain in vivo. (A-C) (A) Carbonyl region after 3.8 h of infusion. (B) An expanded plot of the GLN C5 peak after 1.1 h and (C) 3.1 h of infusion. In vitro spectra of the brain extract at endpoint. (D) A $^{13}$C spectrum of the GLN C5 region. (E) An $^{15}$N spectrum of the [5-$^{15}$N]GLN region. In the proton-decoupled, NOE-enhanced spectrum, the peaks are inverted due to the negative gyromagnetic ration of $^{15}$N.

Methods of studying a metabolic pathway are provided. The methods comprise providing a quantity of a reporter molecule hyperpolarized by Dynamic Nuclear Polarization ("DNP"), introducing the quantity of the reporter molecule to a subject, and imaging a target substance by NMR spectroscopy, wherein the target substance is a constituent molecule in the studied metabolic pathway. The metabolic pathways studied include the mammalian tricarboxylic acid cycle, and reporter molecules used include hyperpolarized glutamine and hyperpolarized acetate.

Kits for studying metabolic pathways, including the mammalian tricarboxylic acid cycle, are provided. The kits include reporter molecules according to the above methods and instructions for their use in a subject.

In addition, NMR imaging agents comprising the inventive reporter molecules are provided. Also provided are pharmaceutical compositions incorporating the inventive reporter molecules in a pharmaceutically acceptable carrier.

DETAILED DESCRIPTION OF THE INVENTION

All references cited herein are incorporated by reference in their entirely as though fully set forth.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), March, Advance Organic Chemistry Reactions, Mechanisms and Structure 4th ed., J. Wiley & Sons (New York, N.Y. 1992), and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present is invention, the following terms are defined below.

Prior art studies of metabolism with $^1$H or $^{13}$C NMR suffer from the drawbacks of little or no spatial localization and prolonged signal averaging that largely preclude the study of dynamics and is severely limited by cost. The present invention opens up an entirely new regime wherein the local status of brain metabolism is interrogated on the time scale of seconds to minutes with unprecedented chemical specificity. The invention provides a new tool of vastly improved sensitivity. NMR studies utilizing $^{13}$C labeled glucose or acetate that separate neuronal from glial metabolism in the intact brain shed light on previously inaccessible neurological mechanisms involved in cognition and task activations underlying behavior.

Brain metabolism and biochemical neurotransmission are closely integrated to undertake numerous end-functions manifested in the intact animals. Over 80% of brain energy is consumed in the glutamine-glutamate cycle. Functional brain mapping techniques like PET, fMRI, MEG, etc. are currently unable to record the events in glutamate neurotransmission at the cellular level of the neuron and glia. The invention relates to non-invasive neurochemical probes that may permit sub-second monitoring of glutamate neurotransmission. Experimentally, this is demonstrated in vivo in the rodent brain by mapping the details of the glutamine-glutamate cycle in the normal brain.

In biology, NMR spectroscopy has yet to reach its full potential for the simple reason of time limitations associated with the high number of transients required to obtain sufficient SNR under biological constraints. In the brain, neurochemical events occur on the spatial and temporal scale of electrical neurotransmission (second to milliseconds), placing significant limitations on current methods of NMR spectroscopy. The present invention is based, at least in part, on polarization to order unity of nuclear spins prior to rapid introduction to the spectroscopic environment of interest, leading to >10,000 fold improvement in SNR for diverse problems of biological importance.

In one embodiment of the invention, the real time metabolism responsible for neurotransmission in the brain is studied by NMR spectroscopy. In an embodiment, the study of real time metabolism may be approached with two different technologies, creating highly polarized nuclei, exceeding the thermal equilibrium polarization determined by the Boltzmann distribution by up to five orders of magnitude.

The first of these techniques, Parahydrogen and Synthesis Allows Dramatically Enhanced Nuclear Alignment (PASADENA), is a chemical method of reaching spin-order of unity within seconds at liquid state temperature using chemical synthesis. The second technique, Dynamic Nuclear Polarization (DNP), is a solid state polarization technique using unpaired electrons to reach a spin order of unity within hours. Both of the techniques are capable of rendering over 10,000 fold signal enhancement which overcomes previous sensitivity limitations of in vivo NMR spectroscopy.

In the PASADENA method of hyperpolarization, parahydrogen is used for creating highly polarized nuclei, replacing the thermal equilibrium polarization determined by the Boltzmann Distribution by polarizations of order unity in a growing variety of molecular species. The parahydrogen gas is used in a chemical reaction (hydrogenation by catalytic molecular addition to the unsaturated bond of a PASADENA precursor) to produce the PASADENA product of interest. In order to preserve the spin correlation between the protons as a unit on to the precursor, without scrambling. The PASADENA phenomenon was invented in 1986 by Bowers and Weitekamp, and creates a non-equilibrium spin order that can be transformed into polarization. The first biochemical application of the technique was reported in 2001. The transfer of this spin order into polarization of a suitable hetero nucleus can be accomplished by either a diabatic field-cycling scheme or by RF pulses, before administration of the hyperpolarized agent to the experimental subject. The chemistry and the spin order transfer takes place at an elevated temperature (40-60° C.) within the hydrogenation reactor. Then the hyperpolarized substance is filtered to remove the rhodium catalyst before NMR experiments, thereby stopping the hydrogenation and removing the toxic component.

The DNP methodology uses low temperature, high magnetic field, and the unpaired electron of selected species (e.g., triaryl radical) to strongly polarize nuclear spins in the solid state. The solid sample is subsequently dissolved rapidly in water to create a solution of molecules with hyperpolarized nuclear spins. The polarization is performed in a DNP polarizer, consisting of a separate superconducting magnet (3.35 T) and a liquid-helium cooled sample space. The DNP process entails irradiating the frozen sample with 94 GHz microwaves. Subsequent to polarization, the sample is dissolved by an injection system inside the DNP magnet and the toxic triaryl radical removed by a membrane filter. The dissolution process effectively preserves the nuclear polarization.

It is now well established that NMR signal is enhanced over 10,000 fold by the PASADENA and DNP methodologies of creating nuclear spin polarization with recent improvements. Regardless of the particular pulse sequence or detection method the sensitivity is proportional to the fractional polarization P of the target spins, for example, $P=1\times10^{-6}$ for $^{13}C$ at equilibrium at 1.5 T and ambient temperature. It is well known that P for a given nucleus is conserved through chemical reactions, relaxing toward the equilibrium value with a characteristic time $T_1$ of up to several tens of seconds for $^{13}C$. Thus, the establishment by any such method of a high value of P allows the corresponding sensitivity enhancement to be transported to any location and chemical species that can be reached on this time scale. Recent work has demonstrated $^{13}C$ polarizations in excess of 20% (P>0.2) for the nascent products of molecular addition of dihydrogen and DNP and sub-second imaging of these products following arterial injection. This polarization decays with a time constant equal to the familiar spin-lattice relaxation time $T_1$ but even after 5 $T_1$ (from 1 to 6 minutes for the molecules proposed) the available signal is still more then 2000 times greater than the equilibrium $^{13}C$ signal. Thus, there is time for the hyperpolarized molecules to be delivered via the blood flow, taken up into extracellular and intracellular volumes, and even metabolized before data acquisition. The signal-to-noise ratio at 5 $T_1$ with hyperpolarization may be achieved with ordinary polarization only after more than 50 days of signal averaging at 1 $s^{-1}$. Thus, the methods of the present invention revolutionize chemically-specific in vivo NMR spectroscopy by making practical a class of observations both broader than and complementary to existing methods. Changes in concentration in the nM regime, occurring in seconds, may be observable for the first time in single shot experiments over volumes of interest in brain studies.

In various embodiments, the present invention also allows for the identification and synthesis of polarizable, non-toxic water soluble molecules enriched in $^{13}C$ wish known functional and targeted roles and long $T_1$ relaxation times, to allow them to carry spin polarization into cells. In addition, the use of fast $^{13}C$ MR imaging and spectroscopy techniques (e.g., for a 4.7 T Bruker Paravision experimental animal NMR spectrometer) is possible, thereby enabling anatomic and metabolic imaging of the fate of molecules identified and hyperpolarized. The invention also includes the uptake and further metabolism into the neuronal-glial glutamate neurotransmitter cycles of hyperpolarized $^{13}C$-contrast agents in the normal brain, with conservation of their enhanced polarization sufficient to provide sub-second $^{13}C$ images and localized spectra with greater sensitivity and specificity than is currently provided by known NMR methods.

$^{13}C$ NMR spectroscopy is a technique which, unlike standard proton spectroscopy, provides dynamic measures of brain metabolism. These include estimates of cerebral tricarboxylic acid cycle rate and glutamate-glutamine cycling from neuron to astrocytes, among others. The natural abundance of 1.1% and lower gyromagnetic ration compared to protons, gives $^{13}C$ NMR substantially less sensitivity, which translates into low SNR. However, $^{13}C$ NMR has high specificity that enables one to visualize carbon positions of several amino acids (e.g., glutamate and glutamine) and other metabolites even at low magnetic field.

Figure 2:
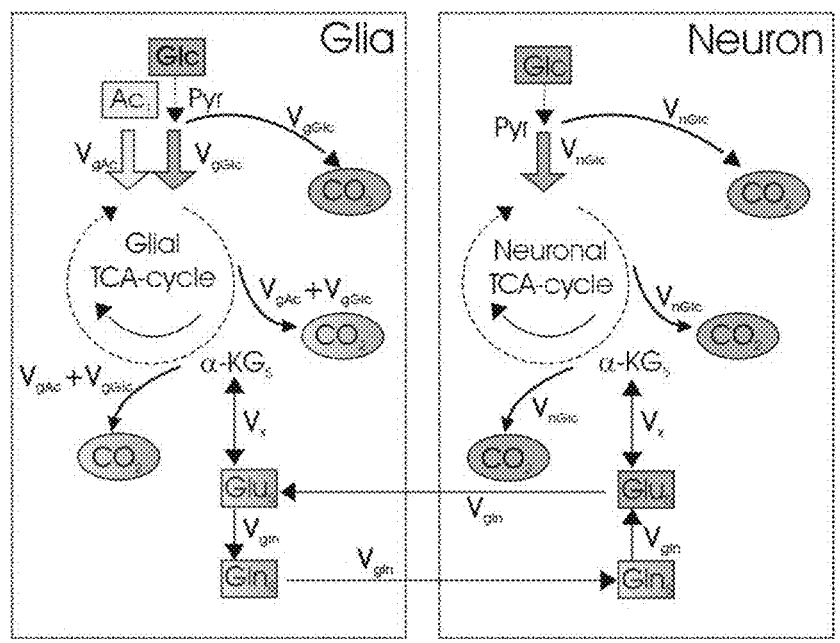
FIG. 2. Metabolic profiles of 1-$^{13}$C Glucose and 1-$^{13}$C Acetate infusion. Synchronous in vivo imaging of neuronal and glial metabolism provides unique access to the process of neurotransmission by following the fate of $^{13}$C enriched fuels preferentially metabolized by neurons (glucose) and glia (acetate) respectively.
Figure 2:
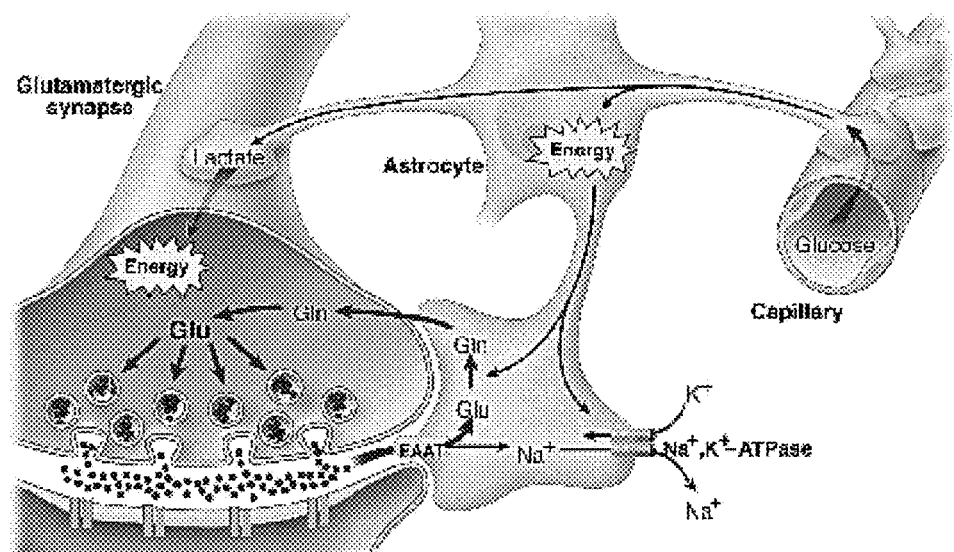
Figure 2:
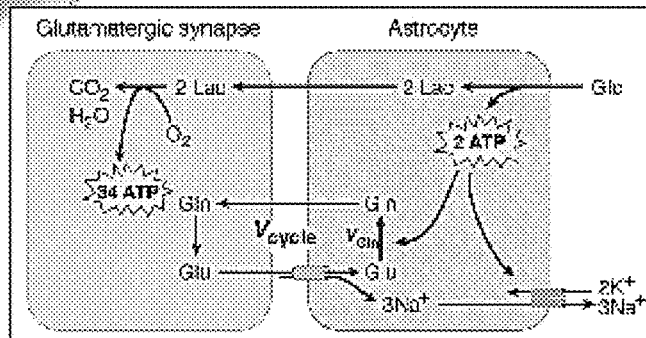

Due to the low $^{13}C$ sensitivity, $^{13}C$-labeled substrates (e.g., D-glucose-1-$^{13}C$, Sodium acetate-1-$^{13}C$) are infused to enhance the MR signal. When the substrate is infused, the high specificity of the $^{13}C$ spectrum can be exploited, and the time course of labeled metabolites can be tracked through important metabolic pathways. The "tracking" takes advantage of well-known carbon exchange through relevant metabolic cycles including the tricarboxylic acid cycle (citric acid cycle). The inventors have had a great deal of experience with $^{13}C$ NMR by measuring tricarboxylic cycle rates of neurons and glia independently in the normal and disease human brain using 1-$^{13}C$-labelled glucose and acetate respectively (FIGS. 2a & b). Road maps of neuronal, glial metabolism in normal brain assist in the design and interpretation of in vivo hyperpolarization studies utilizing either hyperpolarized $^{13}C$ glucose, $^{13}C$ sodium acetate or TCA cycle intermediates fumarate and succinate. The neurochemical significance of these pathways and the central role in explaining the observations made with functional MRI (fMRI) is discussed in several reports and shown in FIG. 2c.

In various embodiments of the present invention, reporter molecules (such as those described in Tables 1 and 2, below) are provided, as well as methods of imaging various substances in the body by providing a quantity of a reporter molecule, introducing a sufficient quantity thereof into a subject, and thereafter imaging a target substance. Suitable quantities of the reported molecule as well as suitable routes of administration of the same to a subject will be readily understood by those of skill in the art, and can vary based on certain well-accepted physiological parameters (e.g., age, weight, sex of the subject, target substance of interest, reporter molecule being utilized, etc.). In various embodiments of the present invention, the aforementioned methods of imaging may be used in connection with a range of applications, including, but in no way limited to, the diagnosis/prognosis of disease or other physiological conditions, the study of biological systems, and the like.

TABLE 1

| Precursor Molecule | Metabolites and Process of Hyperpolarization | $T_1$ of the Product |
| --- | --- | --- |
| A. NaO\C$^{13}$=O / D$_2$C | Hyperpolarized acetate (DNP) | 45 s |
| B. D, D, D, D, H$_2$N structure with C$_{13}$, NH$_2$, OH | Hyperpolarized glutamine (DNP) | 40 s |
| C. D, D, D, D, H$_2$N$_{15}$ structure with C, N$_{15}$H$_2$, OH | Hyperpolarized glutamine (DNP) | 50 s |

In alternative embodiments, a kit for use in connection with MR imaging is provided. The kit is an assemblage of materials or components, including at least one of the inventive reported molecules; more specifically, a composition comprising a quantity of at least one of the inventive reporter molecules, as described above.

The exact nature of the components configured in the inventive kit depends on its intended purpose. For example, some embodiments are configured for the purpose of diagnosing specific diseases, while others are useful in connection with studying biological processes unrelated to healthcare needs (e.g., studying metabolic pathways). In one embodiment, the kit is configured particularly for the purpose of diagnosing or prognosing a medical condition in a mammalian subject. In another embodiment, the kit is configured particularly for the purpose of diagnosing or prognosing human subjects.

Instructions for use may be include in the kit. "Instructions for use" typically include a tangible expression describing the technique to be employed in using the components of the kit to effect a desired outcome, such as to diagnose or prognose a physiological condition. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable way that preserves their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferable to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition including a quantity of one or more reporter molecules. The packaging material generally has an external label which indicates the contents and/or purpose of the kit and/or its components.

In various embodiments, the present invention provides pharmaceutical compositions including at least one of the inventive reporter molecules along with a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

Still further embodiments of the present invention are directed to drug discovery technology using the inventive reporter molecules. The reporter molecules of the invention may be used, for example, in connection with animal trials of novel therapeutic compounds to study the compounds' efficacy or other physiological properties of interest in screening drug candidates or in amassing otherwise valuable information about a particular therapeutic compound. Techniques and protocols for doing so will be readily ascertainable by those of skill in the art, and can be implemented without undue experimentation.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

In Vivo $^{13}$C PASADENA Imaging

Figure 3:
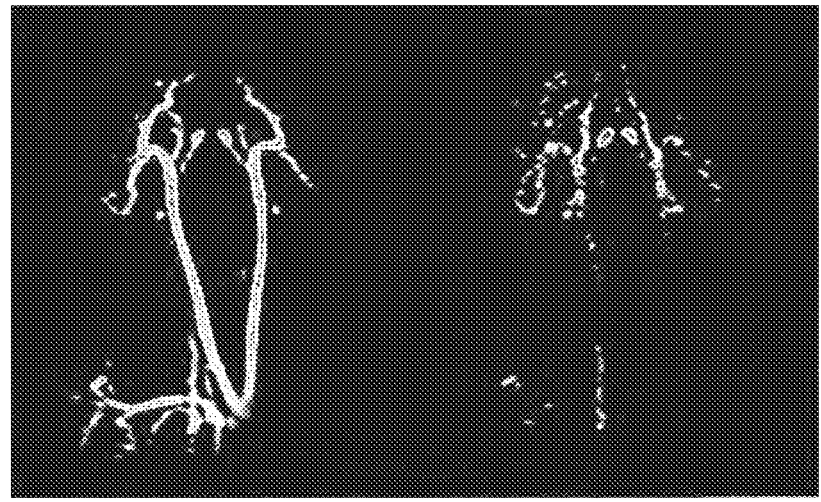
FIG. 3. Real-time $^{13}$C PASADENA images of carotid artery and major blood vessels of the pig brain. Two of a time-lapse series of images obtained subsequent to a single injection of aqueous hydroethyl propionate (1, $^{13}$C) with initial polarization P=0.4.
Figure 4:
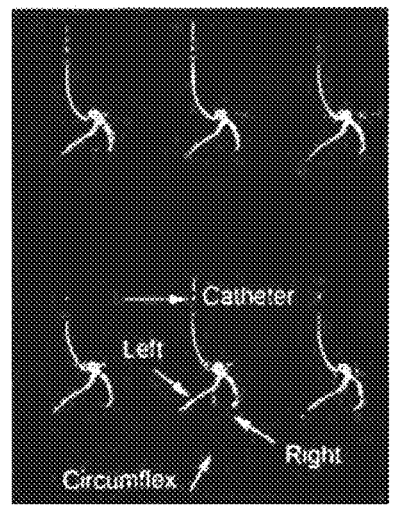
FIG. 4. Cine views of coronary arteries of a pig: left, circumflex and right. Each frame was acquired in less than one second employing PASADENA FIG. 5. Hyperpolarized $^{13}$C imaging at 1.5 T. Left: Sub-second 3D $^{13}$C FIESTA image of 3 ml syringe of hyperpolarized $^{13}$C hydroxyethylpropionate. Note the Gibbs ringing, visible due to the high SNR. Center: Decay of $^{13}$C hyperpolarized signal over time: Signal vs. time plot of the average of all pixels in the ROI for each of 12 acquisitions of $^{13}$C hydroxyethyl propionate. Time courses of $^{13}$C signal decline measured in $^{13}$C hydroxyethylpropionate. Time courses of $^{13}$C signal decline measured in $^{13}$C hydroxyethylpropionate and sodium maleate in arbitrary units (a.u.) were similar. Right: Hyperpolarized reagent concentration titration. 3 ml syringes of titrated concentrations of hyperpolarized $^{13}$C hydroxyethyl propionate were imaged in the surface coil with a 4.25M phantom of 1-$^{13}$C labeled acetate to serve as signal and spatial reference phantom. We were able to detect signal as low as 0.1 mM. At a concentration of 0.64 mM, the absolute signal of the PASADENA reagent was equivalent of 4.25M of $^{13}$C signal from the reference phantom thereby confirming signal enhancement of over 6,000 times.

Utilizing a PASADENA polarizer, the inventors injected hyperpolarized $^{13}$C-molecules in rats. Transmitting at the $^{13}$C-frequency, images were acquired using TrueFISP pulse sequences, 3D FIESTA (acronyms for transient versions of so-called steady state free procession image sequences) and fast CSI (chemical shift imaging) sequences. Examples of $^{13}$C images acquired utilizing PASADENA hyperpolarization (FIGS. 3-4) were produced using $^{13}$C-labeled hydroxyethyl acrylate which on hydrogenation forms hydroxyethyl propionate.

Sub-second carbon imaging is greatly simplified when the signal of interest exceeds the background signal from natural abundance resonances. This is possible when a $^{13}$C hyperpolarized agent is injected. Substantially enhanced images can be acquired during an interval several times the $T_1$ of $^{13}$C polarization. Long $T_1$ (in excess of ten seconds) is obtained for $^{13}$C in small molecules at sites where there is no directly attached proton. Deuteration can be used to achieve this (e.g., glucose) and it occurs naturally for carbonyls. The measured $T_1$ for the proposed molecules are listed in Table 2. Enhancements in excess of 1000 from hyperpolarization are obtained in the first 5 $T_1$ (i.e., imaging and spectroscopy experiment should be accomplished within 100-225 seconds after hyperpolarizing the molecules). For the molecules proposed, the hyperpolarization decays with a time constant of 20-45 seconds ($T_1$ relaxation time of the agent) and therefore long scan times are not feasible. In order to overcome this problem, the inventors have successfully reprogrammed several fast imaging pulse sequences with multinuclear capability (multinuclear pulse sequences, broadband amplifier, and multinuclear coils).

Figure 5:
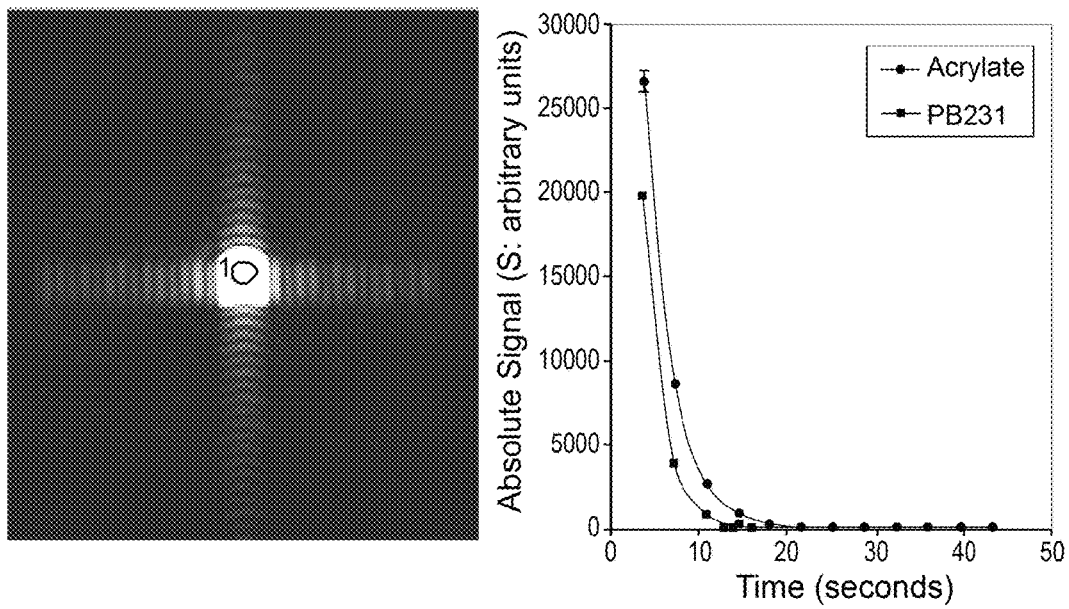
Figure 5:
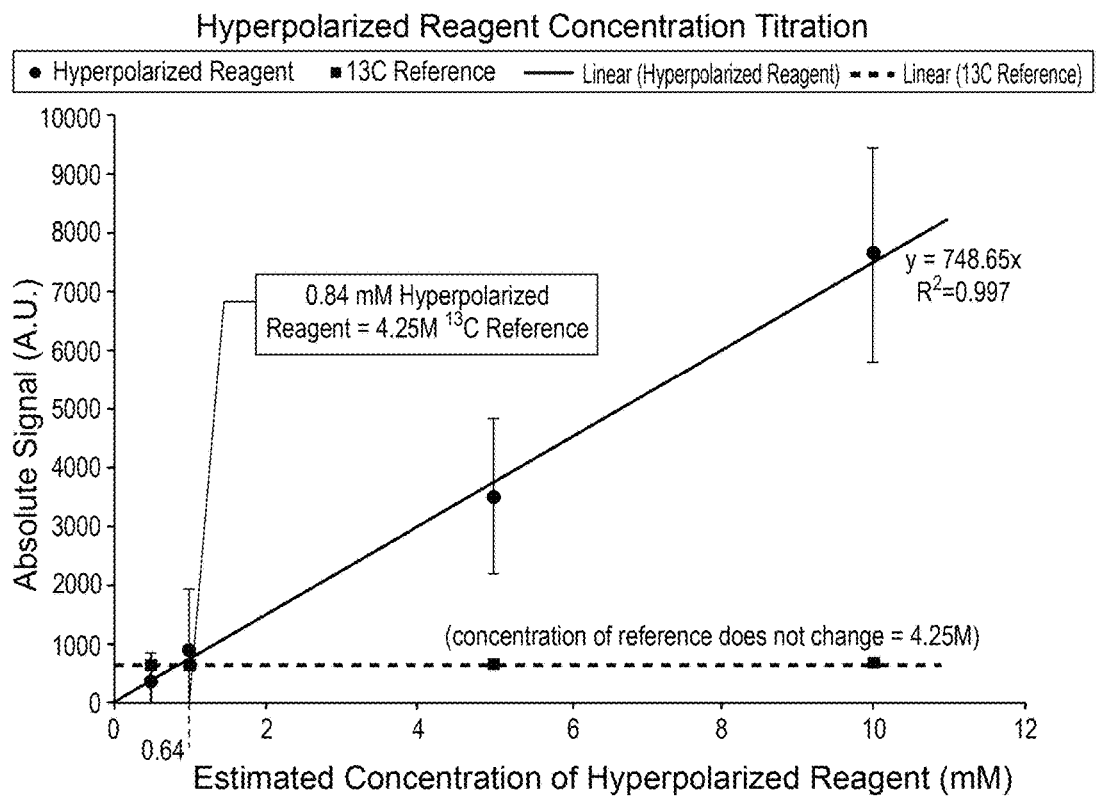

Syringes containing hyperpolarized $^{13}$C reagents were imaged immediately (FIG. 5, left) demonstrating the dramatic signal enhancement. The visible Gibbs ringing phenomenon resulted in part from the low imaging matrices used in this study; it is accentuated by high SNR resulting from the ten thousand-fold increase in $^{13}$C signal magnitude resulting from PASADENA in vitro. Two PASADENA hyperpolarization agents (hydroxyethyl propionate and sodium maleate) were imaged demonstrating similar signal enhancement and time courses (FIG. 5, middle). Furthermore, the inventors wished to determine the lowest detectable concentration of hyperpolarized reagent that could be used on a 1.5 T system. They performed a titration curve as shown in FIG. 5 (right). Using the FIESTA pulse sequence, the inventors have detected a signal as low as 0.1 nM. Further improvements that may be accomplished in various embodiments of the present invention are discussed below.

Figure 6:
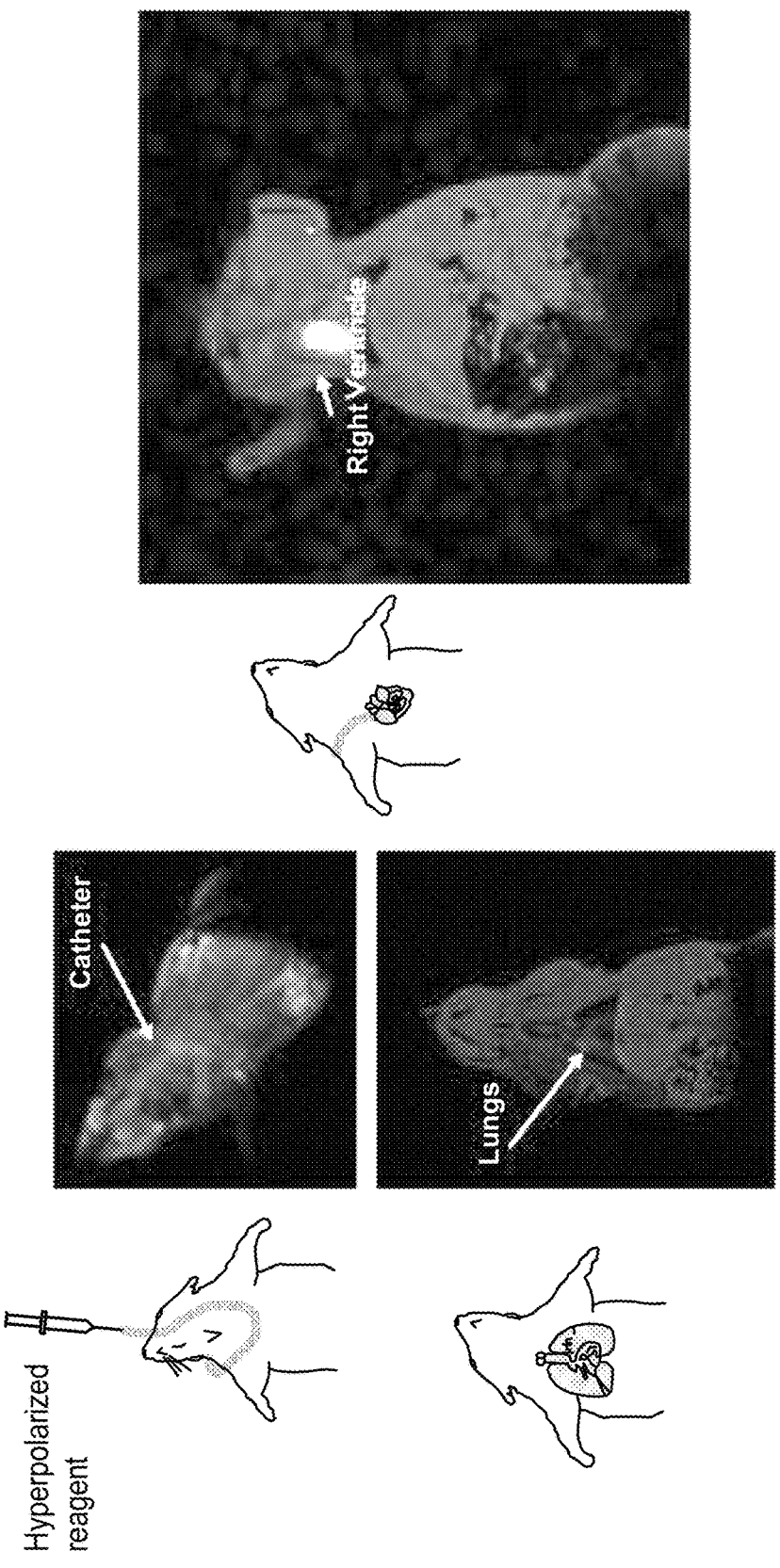
FIG. 6. Real time 3D $^{13}$C in vivo rodent imaging with PASADENA. Hyperpolarized $^{13}$C imaging reagents were administered via jugular vein, and the resulting ultra fast $^{13}$C MR images displayed as overlay on proton images of the same animal. The advantage of 3D FIESTA is the ability to reconstruct 3D images as shown in A) images of the catheter, as well as several slices in the same experiment thereby demonstrating enhancement of the B) lungs and C) heart.

In vivo $^{13}$C imaging of hyperpolarized reagents was accomplished on twelve rats sedated with a cannula introduced into the right jugular vein. A syringe containing hyperpolarized $^{13}$C reagent was connected and immediately injected after hyperpolarization while $^{13}$C imaging was in progress. After rapid injection of hyperpolarized $^{13}$C imaging reagent, 3D FIESTA images capture the same structures in $^{13}$C images, each acquired in 0.31 seconds. The supplying catheter, right atrium and right ventricle, the left ventricle of the heart and the left and right lung were observed with $^{13}$C imaging as indicated in FIG. 6.

These results demonstrate that imaging can be accomplished 1) using fast, sub-second $^{13}$C MRI, 2) visualizing hyperpolarized reagents in three dimensions, 3) over time, and 4) in vitro and in vivo.

Example 2

In Vivo Spectroscopy

Figure 7:
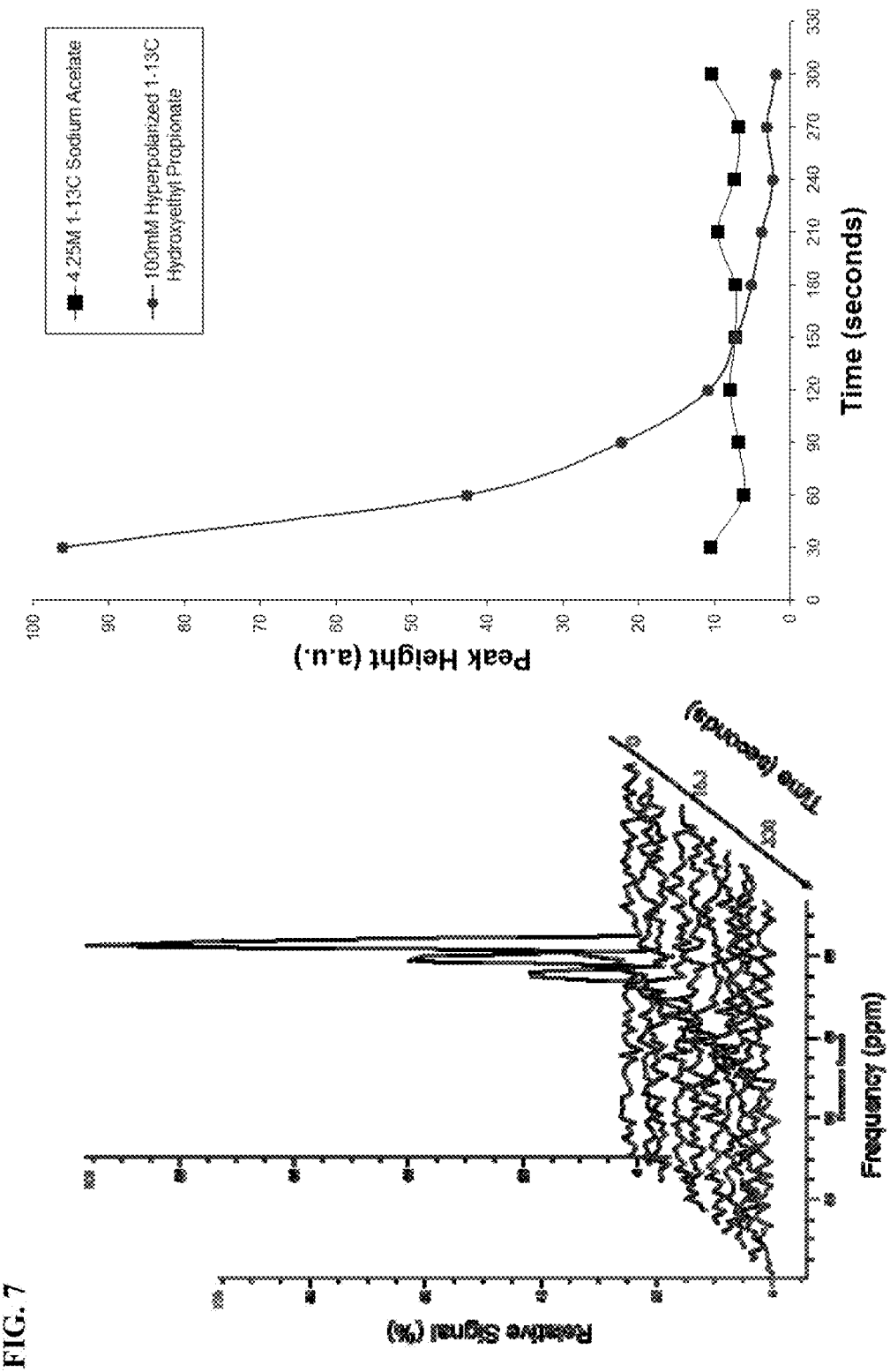
FIG. 7. Time course of $^{13}$C CSI of hyperpolarized $^{13}$C reagent. $^{13}$C CSI readily demonstrate acquisition of the hyperpolarized signal with correct chemical shift (left) and demonstrable increase in SNR (right).

The inventors have used $^{13}$C labeled isotopes of intrinsic biological molecules, such as glucose, which are metabolized in the body via the TCA cycle that can be tracked with MR spectroscopy. This allows the elucidation of biochemical processes such as glutamate neurotransmission and metabolite synthesis rates in vivo. However, based on the Boltzmann distribution, $^{13}$C NMR suffers from inherently low SNR, requiring the use of lengthy pulse sequences which limits its use due to heat deposition and the instability of the subjects over literally hours of scan time. This is where hyperpolarization demonstrates strong potential. The low SNR issues are overcome by polarization up to 26,000 times greater SNR as demonstrated above. One of the challenges of hyperpolarized imaging is the need for fast spectroscopy sequences due to the fast relaxation of the hyperpolarized signal. Therefore the inventors developed fast chemical shift imaging techniques that allow for the simultaneous acquisition of both spatial and spectral information. $^{13}$C CSI was acquired of injected $^{13}$C-labelled hyperpolarized hydroxyethyl propionate and, simultaneously, of a 4.25 M acetate phantom (FIG. 7). Both 2D spectral reconstruction and metabolic maps were successfully generated from the proton and carbon-13 data acquisitions.

Figure 8:
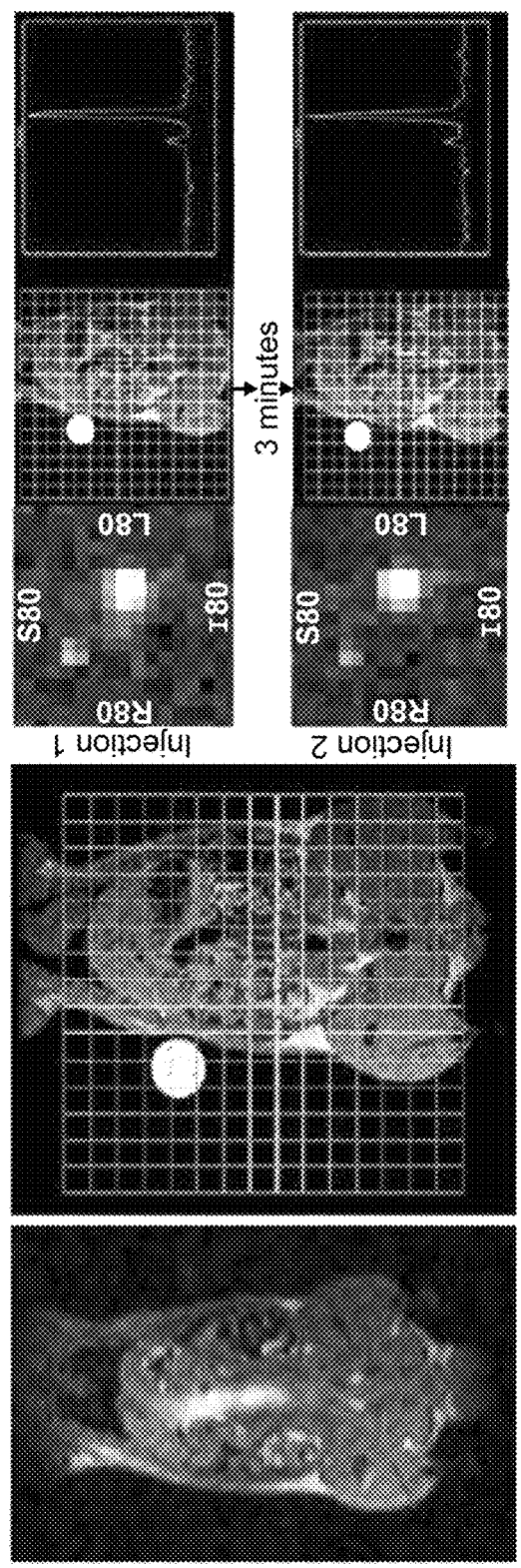
FIG. 8. Left: $^{13}$C MRI of hyperpolarized $^{13}$C reagent injected into a cannula placed at the entrance of the femoral artery. The vena cava of the rat can be seen enhanced in the $^{13}$C images. Middle: $^{13}$C CSI of the same experiment. The CSI grid is overlaid over $^1$H image demonstrating accurate localization of the CSI data. CSI provides the additional information of chemical shift. Right: $^{13}$C CSI acquired with 1st injection (top) and 2nd injection three minutes later (bottom). These results demonstrate that not only can we capture morphological and chemical information but dynamic time series information as well.

Good results were achieved in in vivo rat studies with fast $^{13}$C CSI. The inventors implanted a catheter in the right femoral vein of the rat so that the reagent would travel up the vena cava as can be seen from the $^{13}$C image of the reagent (FIG. 8, left). As expected, the inventors observed a signal in the CSI from the reference phantom and from the vena cava of the rat (FIG. 8, middle). Furthermore, due to the fast data acquisition times, measurements were also taken in vivo after a second injection of hyperpolarized reagent, thereby providing dynamic and repeatable time course (FIGS. 7 and 8, right). Thus, the invention includes a fast $^{13}$C CSI pulse sequence that can accurately detect $^{13}$C signal with measures of (1) signal intensity, (2) anatomical location, (3) chemical shift, and (4) dynamic and repeatable time course.

Example 3

Identifying Hyperpolarization Precursors

PASADENA: Directed synthesis of PASADENA precursor molecules, suitably enriched with $^{13}$C, provides nontoxic tracking reagents with known desired biological properties, including in some cases intracellular transport and metabolism. New reagents may be necessary for the versatile implementation of PASADENA imaging and spectroscopy. Identifying molecules to introduce parahydrogen in biological systems is a feature of the invention.

The PASADENA precursors may have at least one of the following features: (1) an unsaturated bond suitable for hydrogenation by molecular addition; (2) a hydrogenation reaction with a time scale that is shorter than the low-field singlet state relaxation times (typically tens of seconds) of the nascent protons on intermediates and products; (3) an isotopically-enriched $^{13}C$ site with scalar coupling to the added protons; (4) water solubility and low toxicity; (5) an ability to be introduced into a specific biological system safety and quickly in times comparable or less than the spin lattice relaxation time of the hyperpolarized spin; and (6) availability either commercially or by custom synthesis.

DNP: Small molecules can be hyperpolarized by DNP, albeit slowly and in the solid state, but this technology is more general than PASADENA, in not requiring synthesis by hydrogenation. The mechanism of DNP hyperpolarization requires the presence of unpaired electrons, which are added to the sample as, for example, an organic free radical. In order for the DNP process to be effective, the radical must be homogeneously distributed within the sample. To achieve this in an aqueous sample, a glass-former (e.g., glycerol or glycol) is added to prevent crystallization and to produce an amorphous solid after cooling the sample. Once the sample is hyperpolarized, it is guided by the similar relaxation mechanisms.

Table 2 summarizes the key facts demonstrating feasible synthesis and existence of sites with long $T_1$. Specifically, the inventors have identified four water soluble biomolecules for hyperpolarization. The four molecules can be either commercially obtained or custom synthesized. In the cases of hyperpolarization by PASADENA, both the precursors and the hydrogenated products are water soluble and the hydrogenation experiments have achieved high yields. $T_1$ times were experimentally determined.

TABLE 2

| Precursor Molecule | Metabolites & Process of Hyperpolarization | $T_1$ of the Product |
|---|---|---|
| A. ![structure] | Hyperpolarized precursor for succinate (PASADENA) | 25 s |
| B. ![structure] | Hyperpolarized glucose (PASADENA) | 20 s |
| C. ![structure] | Hyperpolarized acetate (DNP) | 45 s |
| D. ![structure] | Hyperpolarized glutamine (DNP) | 40 s |

Since nuclear spin polarization survives enzymatic conversions which occur in the body, once the initial reagent has been administered, there are also advantages to carrying the spin order into the metabolic cycle as $^{13}C$ polarization (taking advantage of the long $T_1$). The efficiency with which polarization is transferred to the metabolic product may be quantified. NMR and metabolic flux indicators may be quantified: the metabolic flux indicators can be dynamically followed by fast $^{13}C$ NMR spectroscopy as will fast $^{13}C$ CSI sequences; both of the capabilities have been well established by the inventors (FIGS. 6 & 7).

A. Starting with non-toxic water soluble $^{13}C$ sodium fumarate and its hydrogenation product $^{13}C$ sodium succinate (hydrogenated from fumarate in 60% yield in initial unoptimized low pressure study), conservation of $^{13}C$ hyperpolarization through mitochondrial-liver Complex II conversion to fumarate may be demonstrated, according to equation 1.

Eq. 1

B. Starting with perdeuterated 1-$^{13}C$ dehydroglucose and its hydrogenated product 1-$^{13}C$ glucose, conservation of polarization through the hexokinase reaction and conversion to glucose-6-phosphate may be demonstrated, according to reaction 2. Glucose, as the principal fuel for the brain, is rapidly transported across the blood brain barrier.

Eq. 2

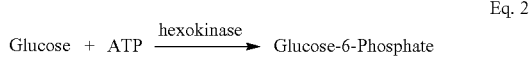

Preliminary results with donated precursors indicate that the hydrogenation of dehydroglucose to glucose can be readily achieved by Rh catalyst in high yield (~85%). Improvements may be readily achieved after optimization of the reaction pressure and temperature. The experimentally determined $T_1$ of perdeuterated 1-$^{13}C$ of glucose is 20 seconds; thereby, the time window of observing the transfer of polarization as the hyperpolarized glucose is metabolized of different TCA cycle metabolites is ~100 seconds (5 $T_1$).

Figure 9:
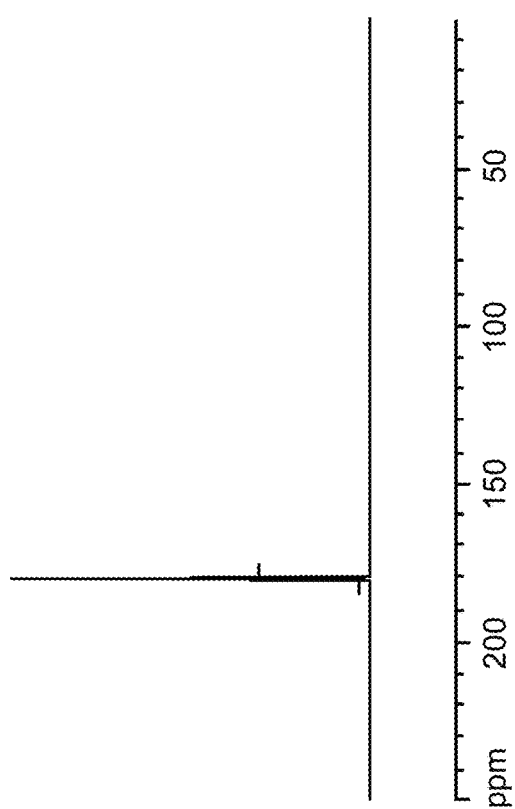
FIG. 9. $^{13}$C NMR spectrum of DNP hyperpolarized CD$_3$ $^{13}$COO$^-$Na using OX63 radical (Sample 1). The SNR from the spectral sequence depicted in FIG. 9 are shown in the corresponding table.
Figure 10:
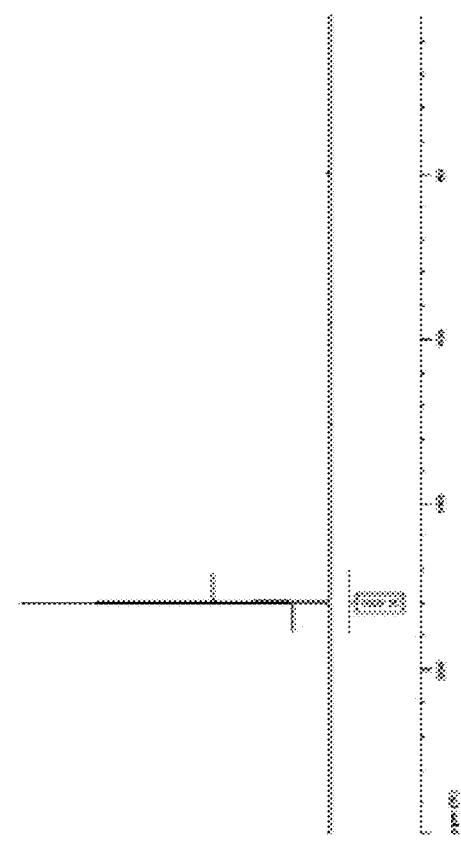
FIG. 10. $_{13}$C NMR spectrum of hyperpolarized CD$_3$ $^{13}$COO$^-$Na$^+$ using Finland radical (Sample 2). The SNR from the spectral sequence depicted in FIG. 10 are shown in the corresponding table.

C. A sample of the proposed molecule, Sodium $^{13}C1$-acetate-$d_3$, was hyperpolarized in water with two different electron donors (FIGS. 9 & 10) in a DNP HyperSense polarizer, and the time course of the decay of the magnetization studied. The SNR obtained from the first spectrum collected from polarized sample 2 is clearly less than that obtained from sample 1, showing that Sodium acetate has a preference for the more polar radical OX63. Both OX63 and Finland are triaryl based radicals and are commercially available form Oxford Instruments, UK. Clearly, the inventors' molecule can render over 10,000 fold signal enhancement by DNP with very long $T_1$ time. The polarization will survive around 325 seconds (5 $T_1$). This allows a large enough time (>5 minutes) window to effectively monitor the first six minutes of uptake and metabolism of hyperpolarized sodium acetate within the glial cells of the rat brain by $^{13}C$ NMR.

D. A sample of the proposed molecule, $^{13}C_1$-$^{13}C_5$ deuterated glutamine, may be hyperpolarized in water with two different electron donors in a DNP HyperSense polarizer and the time course of the decay of the magnetization studied. Glucose, acetate and glutamine can thus be hyperpolarized by two differing methodologies. When coupled with a traditional high resolution NMR spectrometer, DNP HyperSense & PASADENA polarizers permit a wide array of real-time chemical and imaging experiments ranging from in vitro enzymology to the most detailed exploration of neurochemistry of the in vivo mammalian brains.

Example 4

Preparation of the Catalyst Solution for PASADENA

Figure 15:
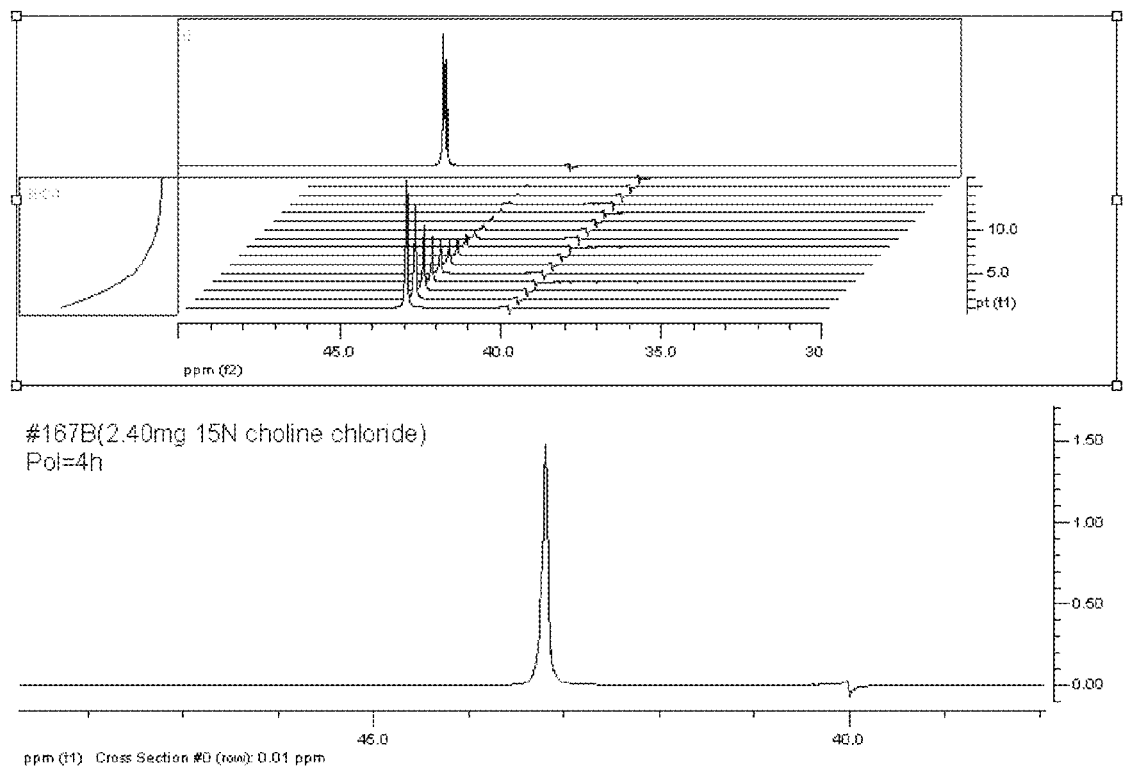
FIG. 15. Preparation of rhodium catalyst solution for PASADENA hyperpolarization.
Figure 15:
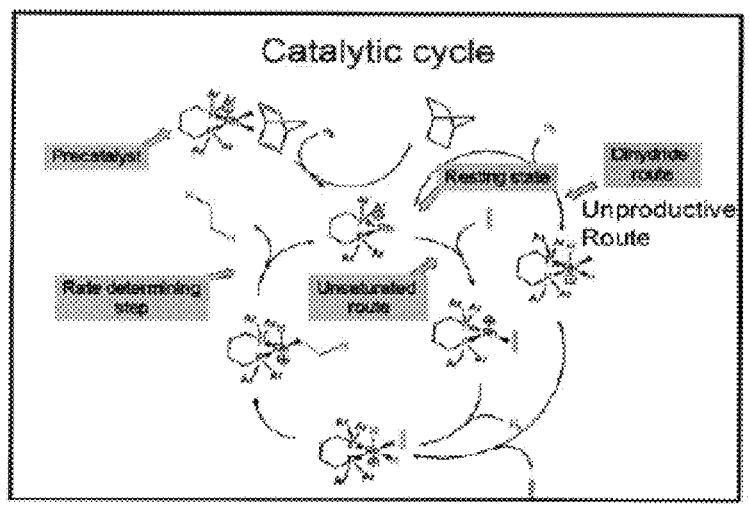

To prepare the catalyst, a water-soluble rhodium compound, $Rh(NBD)_2CF_3SO_3$ (A) and a bisphosphine (B) ligand, were used. The catalyst is preferable 1.3 mM with respect to rhodium and 1.43 mM with respect to the phosphine ligand. De-aerated water is used for MRI experiments, while de-aerated $D_2O$ is employed for NMR-spectroscopy. A calculated amount of the bisphosphine is placed in a glass flask fitted with a magnetic stirrer and a septum. The flask is evacuated through a syringe needle after which water is added through the septum. After dissolution, an inert gas atmosphere is introduced and the rhodium compound, dissolved in a small amount (0.5-1 ml) of acetone, is added with a syringe. The resultant solution is stirred under vacuum to remove the acetone. (See FIG. 15)

Example 5

Generality of the Catalysis of Hydrogenation

The catalysis of hydrogenation by molecular addition to double and triple bonds between carbons is a general and non-specific chemical reaction described in the literature in great detail. For the specific catalyst described above (water-soluble rhodium norbornadiene bisphosphine), the initiation step involves the dissociation of the norbornadiene moiety upon hydrogenation with dihydrogen. This creates a vacant position in the rhodium complex which serves as the active site for catalysis. The double/triple bonded chemicals bind to this active catalyst and are hydrogenated by excess hydrogen via an addition reaction which is crucial for transferring the spin order of polarization to the hydrogenated product. The excess of parahydrogen is maintained by the high pressure (10 bar) of the gas within the reactor in the polarizer. High pressure of parahydrogen also prevents the unproductive dihydride route. The yield of hydrogenation for the molecules can be quantified and followed by both $_1H$ and $_{13}C$ (in case of labeled molecules) NMR spectroscopy. The invention also relates to the development of novel and versatile water soluble catalysts for the hydrogenation reactions.

Example 6

Theoretical Development and Quantification of Polarization in PASADENA

Appropriate pulse sequences may be readily designed for enhancing proton polarization and transfer of polarization from proton to the hetero-nucleus ($^{13}C$) (currently P=0.2-0.4), within the PASADENA polarizer, there achieving 10,000-100,000 fold gain in $^{13}C$—SNR.

The efficient transfer of the parahydrogen spin order to a third target nucleus via the network of scalar couplings was proposed and quantitatively simulated for systems of a few spins in the original PASADENA proposal. If the target spin is also a proton, a train of pi pulses effectively eliminates the chemical shifts and leaving only the full scalar coupling, including flip-flop terms to share the scalar order with the target spin. Free evolution with the chemical shifts restored provides the symmetry breaking so the a hard π/4 cam elicit an antiphase signal. The focus here is on methods to transfer the singlet order of the proton pair to a heteronucleus through the network of scalar couplings. The bulk of the experimental work on hyperpolarizing heteronuclei via PASADENA has largely relied on less efficient rate processes for the polarization processes rather than tailored unitary evolution under heteronuclear pulse sequences. The first suggestion for efficient heteronuclear polarization was to induce an effective multiple-pulse Hamiltonian with IS flip flop terms. In the present invention, the inventors build instead on the strategy of synthesizing the molecule in low field and later observing it in high field. The best results are obtained by carrying out the reaction in a field which is conveniently low, yet high enough to design the pulse sequences within the usual (multiply) rotating frame approximation, in which the different isotopes are separately addressable by choice of irradiation frequency. The task of developing efficient polarization transfer sequences has been revived in this context and efficiencies approaching unity are possible for polarizing the target heteronucleus. In one embodiment of the present invention, the inventors exactly simulate the polarization transfer from scalar order on the two nascent protons to Zeeman order on the target heteronucleus for all of the inventive molecules and use these simulations to determine the best polarization transfer sequences in the reactor with a minimum of experimentation. This effort is largely numerical. The inventors have implemented the public domain NMR simulation program GAMMA and have used this object-oriented approach to construes the spin density operator of the nascent product molecules as the tensor product of the scalar order and Zeeman order on the various spins. The evolution of this density operator under the various known approaches to such polarization transfer allows optimization of the pulse sequence to be applied in the reactor for each target molecule. The advantage of this approach is that the GAMMA program is written in a superoperator formalism in which relaxation phenomena may be incorporated readily.

Experimental confirmation of these numerical optimizations may be achieved by PASADENA with polarization transfer in the reactor volume. The predicted dependence on pulse timing will be compared to the simulation for a limited number of points. To minimize reagent costs, the bulk of this work may be done with natural abundance precursors. The resulting spectra may generally contain contributions from isotopomers other than the one being optimized, but this is readily simulated and the contribution of these extraneous hyperpolarized signals will typically be small for pulse sequences optimized for a particular isotopomer. This may also serve as practice in the procedure of removing the automatically loaded syringe from the reactor and injecting it into the coil volume of the NMR spectrometer. A phantom will take the place of the rat for this testing. This injection step can be achieved in a few seconds with a timing uncertainty of less than a second, which is far shorter than the target spin $T_1$ for the molecules of interest.

Figure 11:
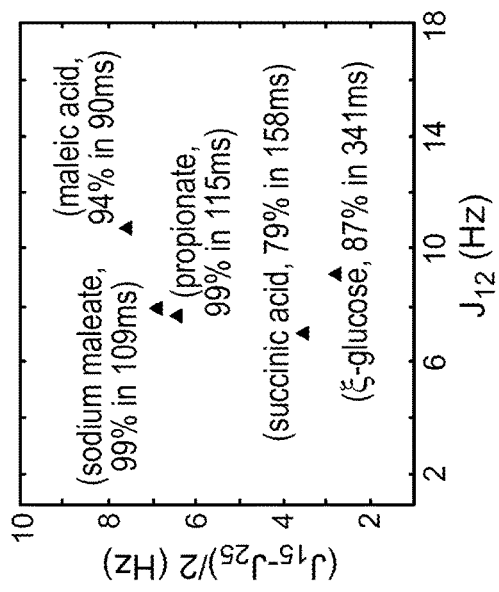
FIG. 11. Preliminary results for calculated polarization transfer to $^{13}$C in the molecules proposed. In all cases the target heteronucleus is bound to one of the two carbons which add the parahydrogen. Where necessary, deuteration is implied to limit the proton spins to those that entered as parahydrogen. The percent polarization stated is for the carbonyl $^{13}$C nucleus. The time it takes to reach the given polarization is stated and is in all cases short compared to the relevant low field spin relaxation.
Figure 12A:
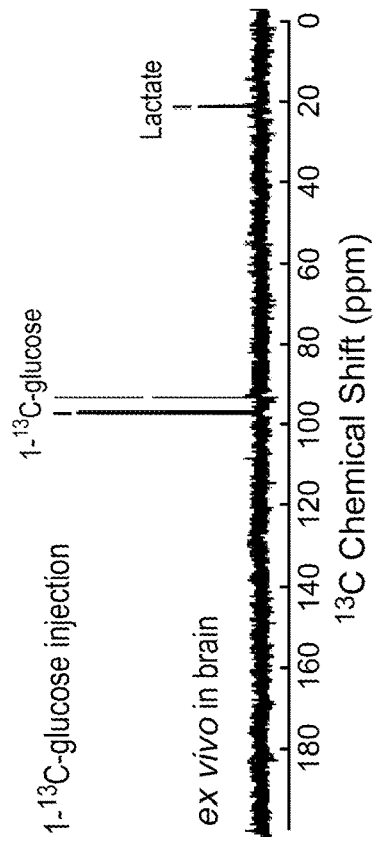
FIG. 12. A: Infusion protocol for 1-$^{13}$C glucose: (i) 600 mg in 3 mL (1.1 M solution by concentration) of 1-$^{13}$C-glucose is injected in rat jugular vain, (ii) blood and brain tissues are quickly frozen in liquid N$_2$ and store at −20° C. Note, the concentrations are measured by peak integration and referencing to 84 mM solution of 1-$^{13}$C-acetate. Spectra acquired with 288-320 scans, TR=8 s at 12 T and 4° C. and processed wish 4 Hz line broadening. B: Infusion protocol for 1-$^{13}$C acetate: (i) 130 mg in 2 mL (800 mM solution by concentration) of 1-$^{13}$C-acetate is injected in carotid artery. (ii) blood and brain tissues are quickly frozen in liquid N$_2$ and stored at −20° C. Note, the concentrations are measured by peak integration and referencing to 84 mM solution of 1-$^{13}$C-acetate. Spectra acquired with 32 scans, TR=60 s at 12 T and 4° C. and processed with 2 Hz line broadening.
Figure 12B:
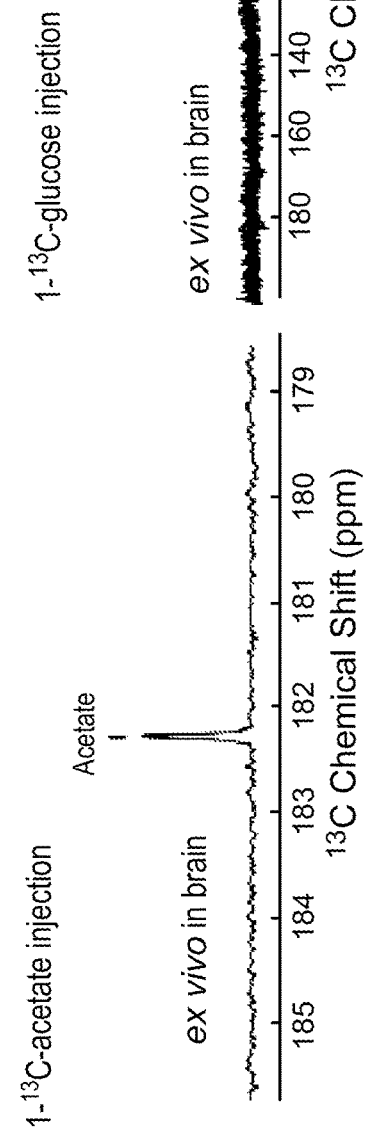
Figure 13:
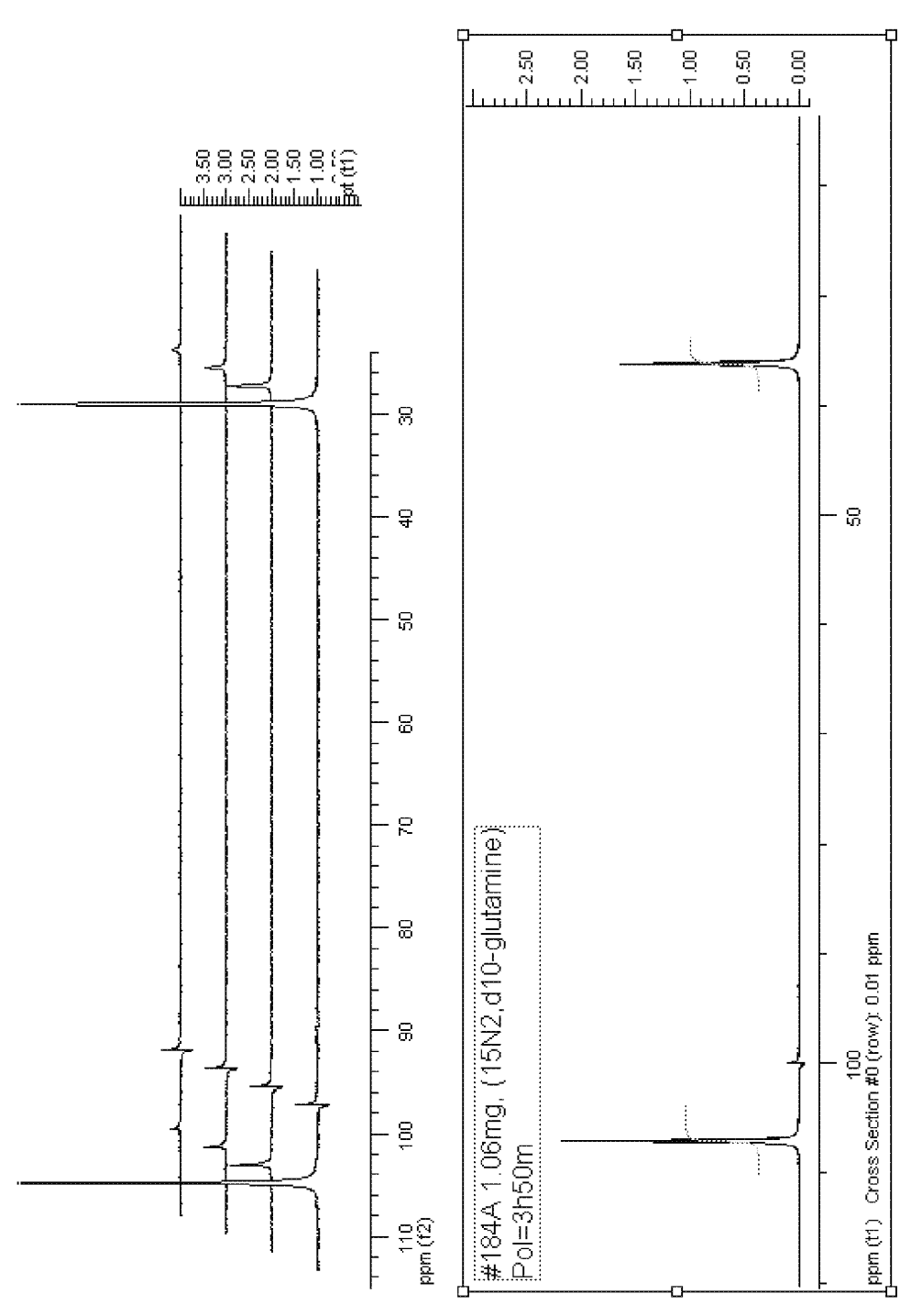
FIG. 13. $^{15}$N NMR spectrum of DNP hyperpolarized $^{15}$N$_2$, d$_{10}$ Glutamine using OX63 radical. Shown is the time resolved decay of the hyperpolarized $^{15}$N signal from two $^{15}$N nuclei in glutamine with two different chemical environments.
Figure 14:
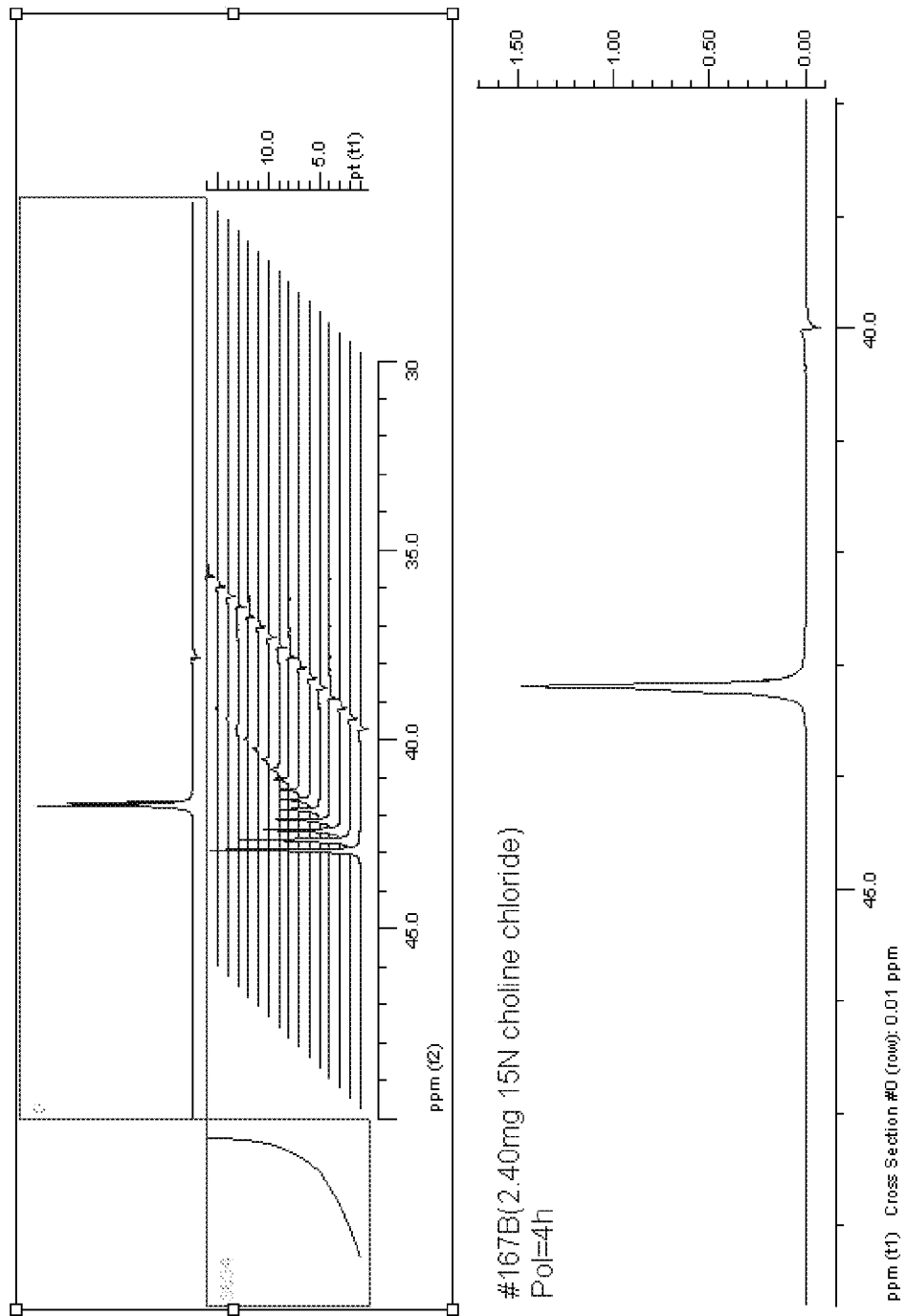
FIG. 14. $^{15}$N NMR spectrum of DNP hyperpolarized $^{15}$N Choline using FINLAND radical. Shown is the time resolved decay of the hyperpolarized $^{15}$N signal.

The optimization of the pulse sequence for three spin system consisting of $^1H1$ $^1H_2$, and S is dependent on the two parameters $J_{12}$ and ½ $(J_{1S}-J_{2S})$ (J: Experimentally obtained J coupling data). Building on the published strategies, the polarization that can be achieved and the time required to execute the pulse sequence has been found for the target isotopomers of some select systems, as illustrated in FIG. 11.

The polarizations observed are no more than half that expected from the ideal unitary evolution. An aspect of the present invention is to unambiguously determine the reasons for the losses and eliminate them if practical. If they are due to proton spin relaxation on the catalytic intermediate or product, this may not be possible, but it has been stated that these times are long enough to contribute little to the observed imperfection. This may be checked experimentally for the molecules shown.

Example 7

In Vitro Monitoring of Enzyme Fluxes

Validation of several of the hypotheses that underlay the instant invention may most economically be achieved by monitoring sample model systems in the presence of perfused enzyme and cofactors: succinic dehydrogenase (succinate), acetate thiokinase (acetate); phosphate activated glutaminase (glutamine). Real time $^{13}C$ NMR may be used to monitor conversion of hyperpolarized $^{13}C$ substrate to its product. Results may be independently compared with standard UV/vis spectroscopic assays.

Example 8

In Vitro Monitoring of Isolated Cells

Starting with perfused cell lines in cultures, a small perfused "brorometer" may be assembled within the bore of the NMR and hyperpolarized precursors may be added to the perfusate. Hyperpolarized product may be detected in "real time" using $^{13}C$ NMR spectroscopy. Neuron and glial cell lines may be incubated individually and then in mixture designed to assay neuron-glial interactions.

Example 9

Ex Vivo NMR Spectroscopy

To check the feasibility of the in vivo biochemical reactions within the time window of hyperpolarization, ex vivo $^{1}H$ decoupled $^{13}C$ MAS spectroscopy of rat brain tissues after 1-$^{13}C$-glucose injection in jugular vein and 1-$^{13}C$-acetate in carotid artery was performed. The glucose and acetate were found to reach 2 and 12 mM concentrations respectively after three minutes from injection which is within the time window of the availability of the hyperpolarized NMR signal.

Example 10

In Vivo Ultra-Fast $^{13}C$ NMR Imaging and Spectroscopy in Rats

Ultra-fast multinuclear imaging and spectroscopy techniques may be used with novel molecules proposed in accordance with various embodiments of the invention and with optimized NMR signal generated by PASADENA and DNP techniques for carbon ($^{13}C$) imaging and spectroscopy to demonstrate sub-second brain images and spectroscopy with hyperpolarized metabolic reagents.

Rats may be lightly anesthetized with ketamine/xylazine for carotid artery/jugular vein cannulation and I-A infusion of $^{13}C$-substrates. During the NMR experiment, a special padded animal cradle holds the anesthetized animal in a comfortable posture in the warmed bore of the magnet. Anesthetized rats may be given intravenous infusion hyperpolarized reagents. At the end of the study, the animal may be euthanized before recovery. Euthanasia is done by overdose of i.p. pentobarbital, as consistent with the panel on euthanasia recommendations. Rats may be Wistar strain, male, 7-9 weeks old. Experiments may be performed using a Bruker PARAVISION NMR spectrometer operating at 4.7 T (Bruker Instruments, Fremont, Calif.) and equipped with Acustar S-150 self-shielded gradient coils (±20 G/cm, 15-cm inner diameter). Rats may be placed in a solenoid $^{1}H$-$^{13}C$ radiofrequency coil with a length of 7.6 cm and an inner diameter of 4.5 cm. Precontrast $T_1$-weighted spoiled gradient-recalled (SPGR) images may be obtained for anatomic locators. After I-V or I-A administration of the hyperpolarized $^{13}C$ reagent, dynamic contrast-enhanced $^{13}C$ MRI may be performed using a $^{13}C$-3D-SPRG sequence, $^{13}C$ FIESTA or $^{13}C$ NMR as described. A study using Gd-DTPA may be conducted using the same protocol, to provide a $^{1}H$ MRI "gold-standard".

The combination of $^{13}C$ MRS detection and substrates selectively enriched in $^{13}C$ in specific positions have made it possible to follow in vivo and in vitro the activity of a large variety of metabolic pathways in cells, and animals which include neuronal glucose uptake, glycolysis, TCA cycle, glutaminolysis, glutamineglutamate cycle, glial acetate uptake, oxidation and glutamine glutamate cycling. Quantitative or qualitative determination of metabolic flux is now possible through a specific step in a pathway, through a whole pathway or through a combination of several pathways. These pathways also provide excellent target for the proposed PASADENA and DNP molecules in the present invention. Since glucose is taken up by the neuronal cells and acetate by the glial cells of the brain; hyperpolarization with over 10,000 fold gain in sensitivity may allow for the modeling signals with kinetics of cellular uptake and metabolism in the brain cells in the first ~100 s of metabolism with sufficient sensitivity, spatial resolution and time resolution. Important interactions between these two dominant cell populations in the mammalian brain are postulated to control many of the important neurochemical processes of higher brain function. Quantitation of the apparent neurotransmitter rate may be possible with the data obtained from simultaneous infusion of hyperpolarized glucose and acetate in rat. One corollary of this research may be the development of more direct, sensitive, and readily interpretable forms of functional magnetic resonance. To date, functional MRI (fMRI) is based on the BOLD mechanism, which provides image contrast via the susceptibility effects attendant to changes in the paramagnetism of hemoglobin associated with its state of oxygen binging. An aim of the invention is to vastly expand real time fMRI by demonstrating new phenomena both more direct and more subtle. While not wishing to be bound by any particular theory, it is believed that, in connection with alternate embodiments of the present invention: (1) the rate of spin-polarized glucose uptake from the capillaries into the neurons of the brain may be imaged; (2) the dynamics of the metabolism of the glucose to neurotransmitter glutamate inside the neurons can be further followed; and (3) hyperpolarized $^{13}C$ acetate can be supplied to the glial cells and the dynamics of these two interacting systems can be correlated simultaneously.

The invention thus includes both detection of the enhanced signals to follow the initial dynamics and direct correlation with the steady-state $^{13}C$ metabolite levels that can be measured with extensive signal averaging using the equilibrium polarization of the $^{13}C$ labels introduced initially in the hyperpolarized state. Normal functioning may be probed by a more direct form of fMRI, in which uptake and metabolism of hyperpolarized glucose is imaged. The immune brain diseases may be differentiated from normal brain on the basis of metabolic flux rates for glucose and/or acetate; the products of metabolism of $^{13}C$ may provide a unique spectral fingerprint, comprised of the sum of metabolism of normal or altered neurons, glia and immune cells. In normal rats, the ability of PASADENA MR imaging to follow rapid changes in neuronal glucose uptake and metabolism may be established in two robust motor and sensory-motor functional tasks, forepaw stimulation and whisker activation. While not wishing to be bound by any particular theory, it is believed that the impact of these functional tasks on glial activation may be tested by quantifying acetate uptake and metabolism.

Example 11

Real-Time Neurochemical Monitoring of Brain Activation In Vivo

It is well established by fMRI BOLD and conventional $^{13}C$ glutamate NMR spectroscopy that motor and sensory activation of the brain results in highly localized changes in blood flow and metabolism. Using hyperpolarized 13C MRI and MRS in whisker barrel stimulation, forepaw movement and light stimuli applied to rats in vivo, the real-time events in these basin activation processes may be explored.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

What is claimed is:

1. A method of studying a metabolic pathway in a subject, comprising:
   providing a quantity of a reporter molecule prepared from a precursor molecule hyperpolarized by dynamic nuclear polarization;
   introducing the quantity of the reporter molecule to the subject; and
   imaging a target substance by NMR spectroscopy, wherein the target substance is a constituent molecule of the metabolic pathway that incorporates the reporter molecule, and wherein the precursor molecule is selected from Formula II:

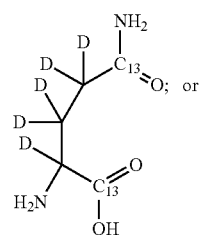

(II)

Formula III:

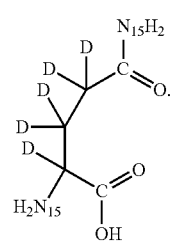

(III)

2. A kit for studying a metabolic pathway in a subject, comprising:
   a reporter molecule prepared from a precursor molecule hyperpolarized by dynamic nuclear polarization; and
   instructions for introducing a quantity of the reporter molecule to the subject and imaging a target substance by NMR spectroscopy, wherein the target substance is a constituent molecule of the metabolic pathway that incorporates the reporter molecule, and wherein the precursor molecule is selected from Formula II:

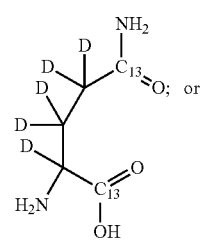

(II)

Formula III:

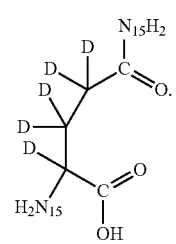

(III)

3. A nuclear magnetic resonance imaging agent produced by the process comprising:
   providing a precursor molecule selected from Formula II:

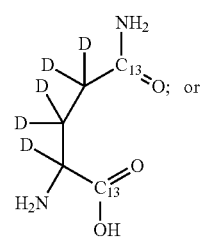

(II)

Formula III:

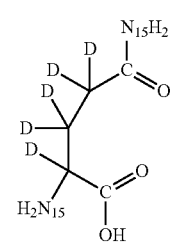

(III)

and
performing dynamic nuclear polarization on the precursor molecule such that the precursor molecule becomes hyperpolarized.

4. A pharmaceutical composition, comprising: a nuclear magnetic resonance imaging agent produced by the process comprising:
providing a precursor molecule selected from Formula II:

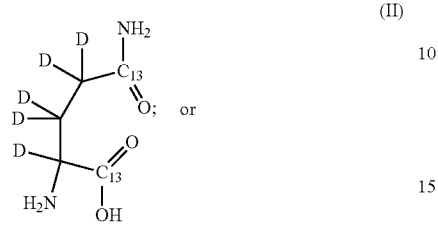

(II)

Formula III:

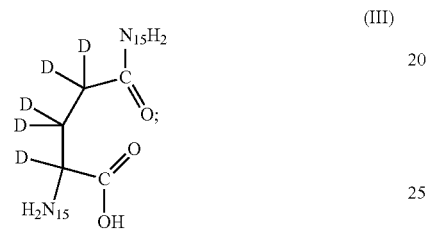

(III)

performing dynamic nuclear polarization on the precursor molecule such that the precursor molecule becomes hyperpolarized; and
a pharmaceutically acceptable carrier.

* * * * *